United States Patent [19]

Fletcher et al.

[11] 4,067,653

[45] Jan. 10, 1978

[54] DIFFERENTIAL OPTOACOUSTIC ABSORPTION DETECTOR

[76] Inventors: James C. Fletcher, Administrator of the National Aeronautics and Space Administration, with respect to an invention of; Michael S. Shumate, Pasadena, Calif.

[21] Appl. No.: 718,266

[22] Filed: Aug. 27, 1976

[51] Int. Cl.² .............................................. G01J 3/42
[52] U.S. Cl. ................................. 356/204; 250/344; 356/246
[58] Field of Search ...................... 250/343, 344, 353; 356/201, 204, 246

[56] References Cited

U.S. PATENT DOCUMENTS

| | | | |
|---|---|---|---|
| 4,011,451 | 3/1977 | Nelson | 356/246 |
| 4,019,056 | 4/1977 | Block et al. | 250/344 |

OTHER PUBLICATIONS

Deaton et al., "Absorption Coefficient Measurements of Nitrous Oxide and Methane", Applied Physics Letters, vol. 26, No. 6, May 15, 1975, pp. 300–303.
Rosengren, "Optimal Optoacoustic Detector Design", Applied Optics, Vol. 14, No. 8, Aug. 1975, pp. 1960–1976.
Garbuny et al., "Laser Engines Operating by Resonance Absorption", Applied Optics, Vol. 15, No. 5, May 1976, pp. 1141–1157.

Primary Examiner—John K. Corbin
Assistant Examiner—R. A. Rosenberger
Attorney, Agent, or Firm—Monte F. Mott; Paul F. McCaul; John R. Manning

[57] ABSTRACT

A differential optoacoustic absorption detector employs two tapered cells in tandem or in parallel. When operating in tandem, two mirrors are used at one end remote from the source of the beam of light directed into one cell back through the other, and a lens to focus the light beam into the one cell at a principal focus half way between the reflecting mirror. Each cell is tapered to conform to the shape of the beam so that the volume of one is the same as for the other, and the volume of each receives maximum illumination. The axes of the cells are placed as close to each other as possible in order to connect a differential pressure detector to the cells with connecting passages of minimum length. An alternative arrangement employs a beam splitter and two lenses to operate the cells in parallel.

9 Claims, 5 Drawing Figures

DIFFERENTIAL OPTOACOUSTIC ABSORPTION DETECTOR

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to optoacoustic detectors, commonly referred to as spectrophones, and more particularly to apparatus for measuring the concentrations of absorbing gases in a sample cell using optoacoustic detection of absorption.

A typical optoacoustic absorption detector consists of a single cell for a sample gas with windows through which a chopped radiation beam passes, and means somewhere in communication with the gas in the cell for measuring pressure variations due to absorption of the beam as it is chopped. Present in the signal derived from the pressure measuring means is the desired increase in pressure due to energy absorbed by the sample gas. Superimposed on the desired increase is an unwanted increase due to energy absorbed by the windows causing an increase in temperature of the sample gas, and therefore an increase in pressure of the gas within the cell. This unwanted increase in pressure may be so large as to mask the desired increase in pressure. Minimization of this unwanted increase in pressure is the object of a copending application Ser. No. 599,284 filed July 25, 1975, now Pat. No. 3,995,960 issued Dec. 7, 1976 and the instant application.

As noted in the aforesaid copending application, there is an increasing interest in detecting trace amounts (approaching 0.01 parts per billion) of atmospheric pollutant gases in an air sample. To minimize the unwanted increase in pressure due to energy absorbed by the windows, a transverse path was created in a single cell optoacoustic detector to substantially cancel the effects of the unwanted window absorption by running the beams through a cross-path having windows that were duplicates of the main path windows. The carrier gas is put in first and the background pressure signal adjusted to as near zero as possible by changing the intensity of one or the other of the beams. When a mixture of carrier gas and sample gas is introduced into the detector, the signal produced will automatically be corrected for the background signal effects, and is a measure of the absorption coefficient of the sample gas.

A prior optoacoustic detector developed by Terrence F. Deaton, David A. Depatie and Thomas W. Walker, was disclosed in a paper titled "Absorption Coefficient Measurements of Nitrous Oxide and Methane at DF Laser Wavelengths," Applied Physics Letters, Vol. 26, No. 6, 300–303 (1975). Two identical cells were used in tandem with a differential capacitance monometer between them. Both cells were first filled with nonabsorbing gas, and the pressure differential between the cells was then minimized while the laser beam was transmitted through both cells in order to "zero" the instrument. Absorption measurements were then made by replacing the carrier gas in one cell with a mixture of the carrier gas and a sample gas. The pressure differential between the two cells represents the absorption coefficient of the sample gas. Residual pressures which are present as background signals due to absorption by the windows of the cell are effectively balanced out by this double cell arrangement.

The problem with the tandem cell arrangement is that extreme care must be exercised in filling both cells to the same pressure during both the zeroing procedure and the measuring procedure. A micrometer driven piston was placed in each cell to change the cell volume for exact pressure balance. The background noise was reportedly reduced to an equivalent coefficient of $3.3 \times 10^{-7}$ m$^{-1}$/W of laser power, which is a factor of 100 times better than what was obtainable with a single cell optoacoustic detector. The problem was that the differential monometer had to be mounted to the side of the tandem cells with unnecessarily long connecting pipes.

Another problem was that due to laser beam expansion, more of the volume in the second cell was radiated than in the first cell. Although the same flux of radiation was passing through both cells in tandem, the response of the second cell was necessarily different from the first due to the different illumination volume, making the problem of adjusting for true differential operation very difficult.

A detailed analysis of the magnitude of the pressure signal expected in an optoacoustic detector has been presented by Lars-Goran Rosengren in a paper entitled "Optimal Optoacoustic Detector Design", which appeared in the August, 1975 issue of Applied Optics, Vol. 14, page 1960. His Equation (1) below is an expression for $P(\omega)$, the rms value of the first harmonic of the pressure in the detector, when the incident optical radiation is chopped at a frequency $\omega$. Assuming a square-wave moldulation and a weakly absorbing gas, this expression becomes $$P(\omega) = \frac{2^{3/2} \beta U \sigma N l Q(\omega) \tau_t}{3\pi V (1 + \tau_c \tau_r^{-1}) [1 + (\omega \tau_t)^2]^{\frac{1}{2}} \{1 + [\omega(\tau_c^{-1} + \tau_r^{-1})^{-1}]^2\}^{\frac{1}{2}}} \quad (1)$$

where $\beta \equiv 3(\gamma - 1)/2$, and $\gamma$ is the ratio of the heat capacity of the gas at constant pressure $C_p$ and constant volume $C_V$; U is the optical power passing through the detector; $\sigma$ is the absoprtion cross section of the gas at the laser wavelength illuminating the detector; N is the density of absorbing gas molecules; $l$ is the optical path length through the detector; $Q(\omega)$ is the acoustical quality of the detector as experienced by the pressure transducer; $\tau_t$ is the thermal relaxation time of the optoacoustic detector; V is the detector volume; $\tau_c$ is the molecular collisional relaxation time; and $\tau_4$ is the radiative relaxation time.

Assuming that $\tau_c << \tau_r$, that $\omega \tau_c << 1$, that the detector has a cylindrical shape of diameter D and length $l$, that the detector is filled with a gas that is for the most part diatomic (air), and that the detector chamber is not acoustically resonant Equation (1) then becomes simplified to $$P(\omega) = \frac{2^{7/2} U \sigma N}{5\pi^2 D^2 [\omega^2 + \tau_t^{-2}]^{\frac{1}{2}}}, \quad (2)$$

since $\beta = 0.6$ for a diatomic gas.

This equation shows that the detector response varies inversely as the square of the chamber diameter, and that the response will be reduced if the chopping frequency is above the thermal cutoff frequency $\omega = 1/\tau_t$.

The number density of absorbing molecules, N, applies only to those molecules actually illuminated by the beam of incident radiation, and the chamber diameter, D, applies to the entire detector volume, including any ancillary volume not illuminated. In order for optimum operation of the optoacoustic detector, it is therefore necessary to minimize the detector diameter, and arrange for as much of the volume as possible to be illuminated by the incident radiation. Furthermore, the chopping frequency should be lower than the thermal cutoff frequency.

SUMMARY OF THE INVENTION

In accordance with the present invention, the problems of the two-cell tandem arrangement are overcome by an arrangement of two side-by-side cells with a differential microphone placed between the two cells, and connected to the two cells through minimum length and diameter passages. The two cells, one of which is a mirror image of the other, are tapered from an opening at one end of predetermined large diameter to an opening at the other end of smaller diameter for the first path of the laser beam. In a folded-beam tandem-cell arrangement, a laser beam through one cell is reflected by two 45° mirrors back through the other cell. A lens in front of the first cell focuses the beam at a point half way between the mirrors. The taper of the cells is selected to conform closely to the shape of the focused beam. In a split-beam, parallel-cell arrangement, the laser beam is split and focused into the two cells in parallel such that the beams in both cells are of the same diameter at the input end of the same diameter at the output end. In either case, both cells are made with the same taper such that the volume for one is the same as for the other. The axes of the side-by-side cells are placed as close to each other as possible in order to connect the differential microphone to the cells with passages of minimum length. This arrangement of tapered cells provides maximum illumination of the sample gas in the cells with a minimum of gas volume.

The novel features that are considered characteristic of this invention are set forth with particularity in the appended claims. The invention will best be understood from the following description when read in connection with the accompanying drawings.

DESCRIPTION OF PREFERRED EMBODIMENTS

Figure 1:
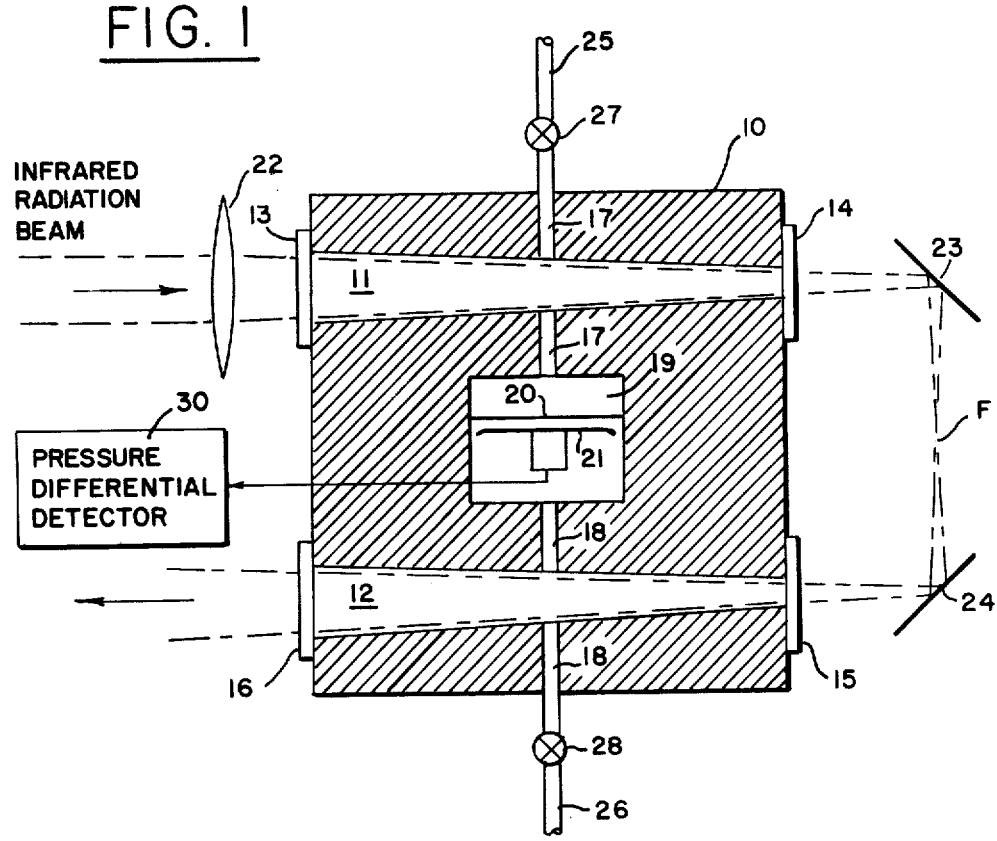
FIG. 1 is a schematic diagram of the folded arrangement of dual tandem cells in a differential optoacoustic detector in accordance with the present invention.

A dual tandem cell arrangement is shown in FIG. 1 for a differential optoacoustic detector 10 in which a mixture of a sample and a carrier gas is placed in one cell 11 at the same pressure as a carrier gas in a second cell 12 for detection of absorption by the sample in the one cell. The two cells are taper-bored in a rectangular metal block along parallel axes with the same predetermined large diameter at one end and the same smaller diameter at the other end such that both cells have the same volume.

Each cell is vacuum-sealed with windows 13, 14, 15 and 16 mounted over the cell openings. The windows are made of a suitable material selected for transmission of light from a monochromatic source, such as barium flouride or zinc selenide for transmission of infrared radiation from a laser. All materials used throughout are suitable for use in high vacuum systems.

Transverse bores 17 and 18 for introducing carrier and sample gas into the cells also connect both of the cells to a differential pressure chamber 19 having a conductive diaphragm 20 and a stationary conductive plate 21. Any pressure differential between the two cells causes the diaphragm to move toward or away from the plate to change the capacitance between the diaphragm and the plate. The change in capacitance is then detected electrically as an indication of pressure differential.

The beam of infrared radiation is focused into the first cell 11 by a lens 22 to conform to the taper of the cell. The beam out of the window 14 is reflected by a first mirror 23 to a second mirror 24 which reflects the beam into the second cell. The focal length of lens 22 is selected such that the principal focus (focal point) F occurs half way between the mirrors. The return beam thus conforms to the taper of the second cell. In other words, the folded beam path for the dual tandem and parallel cells is such that the shape of the beam through the first cell is a mirror image of the shape of the beam through the second cell. This permits both cells to be of the same illuminated volume, and permits the volume of each cell to be a minimum for the shape of the beam.

Gas-fill lines 25 and 26 are connected to the transverse bores 17 and 18 by values 27 and 28. A nonabsorbing carrier gas is allowed to flow through the valves into the cells 11 and 12 at the same pressure by connecting the lines 25 and 26 to the same source of carrier gas. The capacitance detected in a pressure detector 30 is then noted for the balanced pressure condition with the beam excitation of the carrier gas only in both cells. The carrier gas is then removed from one of the cells, preferably the second cell, and a mixture of the carrier and a sample of gas (polluted air, for example) is introduced into the cell at the same pressure as the carrier in the other cell. This may be accomplished by nulling the output of the pressure detector 30 without any radiation into the cells. Once an infrared radiation beam is introduced into the cells, any differential pressure will be due to absorption by the sample gas.

Figure 2A:
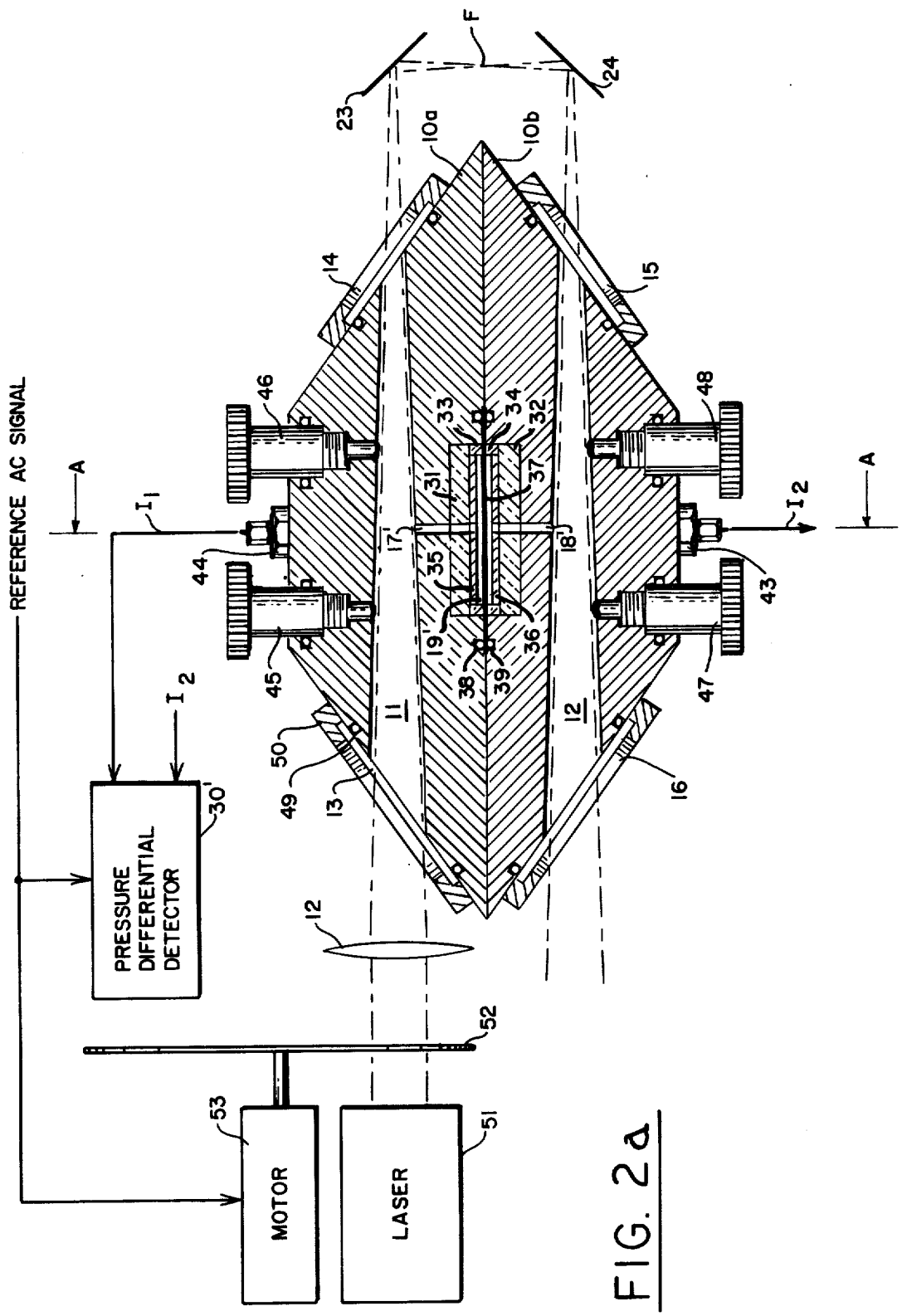
FIGS. 2a and 2b are sectional views of an exemplary embodiment of the dual tandem cell arrangement of FIG. 1.

Referring now to a preferred embodiment illustrated in FIG. 2a, components corresponding directly with components indicated in FIG. 1 are identified by the same reference numerals as in FIG. 1. Other components, although similar in some cases to components in FIG. 1, are identified by unique reference numerals, or by primed reference numerals. In this preferred embodiment, the block is comprised of two parts: a first metal part 10a having the cell 11 formed as a tapered bore as before; and a second metal part 10b having the cell 12 formed as a tapered bore, again as before. A significant different is that the corners of the two parts are cut at an appropriate angle (Brewster's angle) to minimize reflection of incident light, polarized parallel to the plane of the drawing, for the material of the windows 13, 14, 15 and 16. For barium flouride, Brewster's angle is about 55°, and for zinc selenide it is about 67° at a wavelength of 10 μm. The angle is measured between the direction of incidence and an axis normal to the surface of the window. This is important in order to minimize loss of forward transmission of light. Otherwise some light may be reflected and lost at the window 13, while the windows 14, 15 and 16 may reflect light back into the cells to unbalance the radiation flux in the two cells.

Another important difference is that in place of the transverse bores 17 and 18 from the outside of the block into a cylindrical differential pressure chamber 19', there are transverse bores 17' and 18' connecting the tapered bore cells 11 and 12 with the chamber 19'. In practice, the two halves of the block, parts 10a and 10b are cut as rectangular blocks. Once the bores for the tapered cells are formed, the corners of the blocks 10a and 10b are cut to receive windows at Brewster's angle, and one half of the cylindrical chamber 19' is bored into each part. Then the bores 17' and 18' are made to provide passages into the chamber 19' from the cells.

Figure 2B:
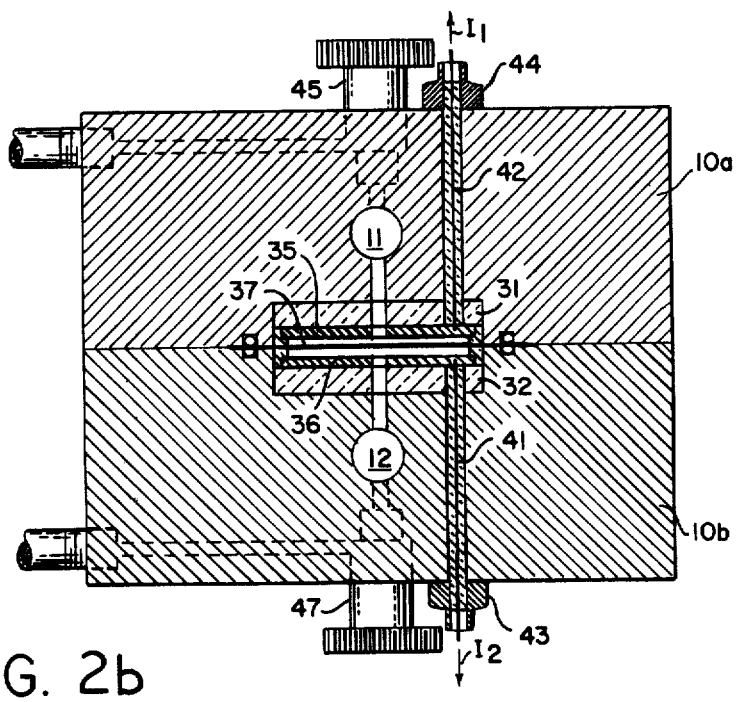

Before assembling the two parts 10a and 10b of the block, annular electrical insulating discs 31 and 32 of nonorganic material, such as glass, are secured in the positions shown, and held in position by rings 33 and 34 of a similar material in order that even from that source there will be no possibility of organic material introducing contaminants into the cells. Annular metal plates 35 and 36, such as gold plates, are mounted on the glass annular discs 31 and 32. These metal plates 35 and 36 form fixed plates of variable capacitors. Secured between the parts 10a and 10b is a flexible diaphragm 37 such as tantalum foil suitably coated on both sides with an inert metal. Both parts 10a and 10b are provided with a very shallow circular recess to receive the diaphragm. The two sides of the chamber 19' separated by the diaphragm 37 are sealed by O-rings 38 and 39. In operation there will be two differential currents $I_1$ and $I_2$ derived from the plates 35 and 36. These currents are conducted through copper leads 42 and 42 shown in FIG. 2b placed in suitable passages (and sealed with glass) out to hermetic feed-throughs 43 and 44. The leads 41 and 42 are connected to plates 35 and 36, and to the center pin of commercial hermetic feed-throughs, such as made by Omnispectra, Model No. 214–8225.

Four valves are provided, two for each cell. A valve 45 is used to introduce a carrier into the first cell, and a valve 46 is used to remove the carrier from the first cell. Similarly a valve 47 is used to introduce a carrier, or carrier and sample mixture, and a valve 48 is used to remove the carrier, or carrier and sample mixture. Each valve is formed as a doubly threaded counterbored hole in an intermediate part of the counterbored hole to receive a threaded shaft turned by a knurled knob. The threaded shaft sits on a shoulder of the counterbored hole. When the threaded shaft is screwed outwardly, i.e., is unseated, a passage connected to an inlet, or an outlet, line is uncovered to permit a carrier, or a carrier and a sample mixed, to pass into the cell. An O-ring provides the necessary seal for each vave while it is open. When the shaft is again seated, the passage is not only covered but more importantly the counterbored hole into the cell is sealed. To assure a pressure seal, a soft metal (indium or gold) washer is placed between the valve seat and the shaft. The end of the valve shaft has a smaller diameter extension protruding through the washer to almost protrude into the gas cells in order to further minimize any space in communication with the gas cell not illuminated by the laser beam. That further increases the sensitivity of the optoacoustic detector, and makes balancing the pressure on both sides of the chamber 19' easier. Once balance is achieved and the valve is closed, tightening of the valve will not decrease the volume of the cell significantly. That is because with metal washers, a seal is not achieved until the shaft has reached its furthest point of entry. Tightening a fraction of a turn will not appreciably change the total volume of the cell.

Soft metal O-rings are also employed to seal the windows against the parts 10a and 10b. For example, an O-ring 49 seals the window 13. The window itself is secured against the O-ring by a bezel 50.

In operation, a beam from a laser 51 is chopped, as by a notched disc 52 rotated by a motor 53 in response to an AC reference signal which is also applied to a pressure differential detector 30' which amplifies for display a signal proportional to the pressure differential between the cells.

Figure 3:
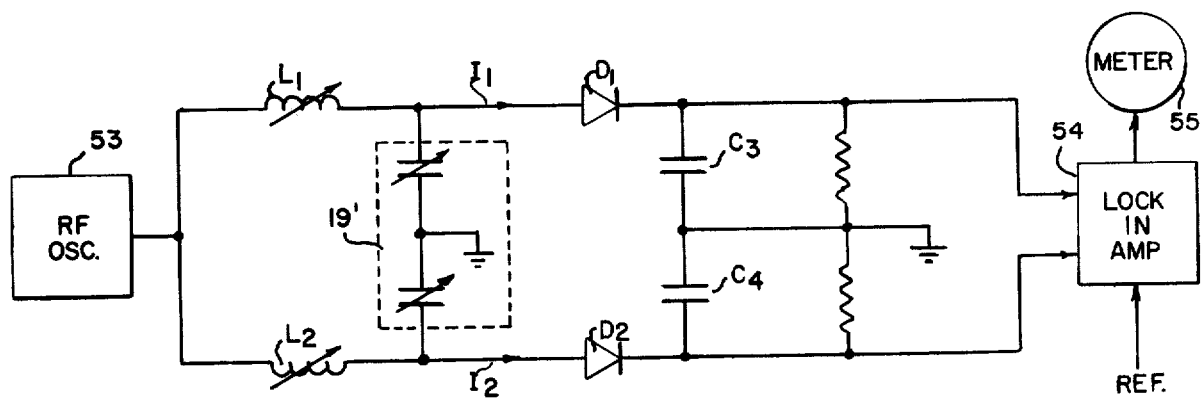
FIG. 3 is a schematic diagram of a pressure differential detector in the system of FIG. 2.

The pressure differential detector 30' is shown schematically in FIG. 3 wherein variable capacitors $C_1$ and $C_2$ represent the variable capacitances between the diaphragm and the plates 35 and 36 of the differential pressure chamber. The chamber is represented in FIG. 3 by a dotted line box around those capacitors which are in two branches of an RF bridge circuit. The other two branches are comprised of variable inductances $L_1$ and $L_2$ used to initially balance the bridge for the radio frequency signal which has been supplied to the bridge from a fixed frequency (RF) oscillator 53.

Diodes $D_1$ and $D_2$ rectify the differential currents $I_1$ and $I_2$, and capacitors $C_3$ and $C_4$ filter the rectified currents. The filtered differential currents are then applied to differential inputs of a lock-in amplifier 54 which drives an ammeter 55 or other suitable display, such as a digital display. In that manner a value proportional to the pressure differential sensed in the chamber 19' is displayed as a measure of the concentration of absorbing gases in the sample cell.

Figure 4:
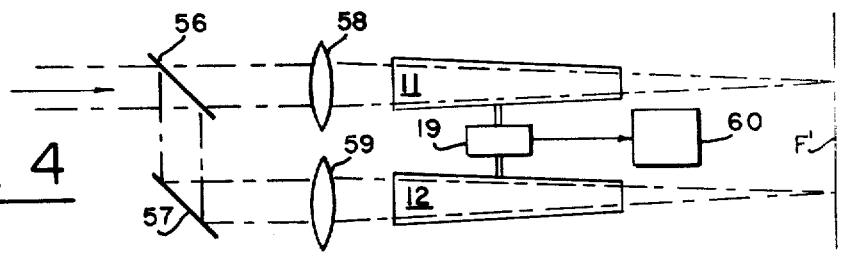
FIG. 4. is a schematic diagram of a variant arrangement.

Referring now to FIG. 4, cells 11 and 12 are shown connected to the pressure differential chamber 19 in a schematic diagram to illustrate a variant in the optical arrangement for directing flux from a laser beam into the cells. A beam splitter 56 directs half ot the flux to a mirror 57. Twin lenses 58 and 59 focus the parallel beams through the cells to the same focal plane F' such that the beam through each cell conforms to the taper of the cell. Any unbalance in the flux intensity for this parallel optical arrangement is compensated in the initial balancing procedure when a pressure differential detector 60 is balanced with carrier gas in both cells at equal pressure.

Although exemplary embodiments of the invention have been described and illustrated herein, it is recognized that modifications and equivalents may readily occur to those skilled in the art, such as modifications in the parallel optical arrangement of FIG. 4 which will make the optical path lengths to the cells equal. Such an arrangement might use a single lens in front of the beam splitter and two pairs of mirrors (one pair of each split beam) judiciously placed not only to direct the split beams through the parallel cells, but also to assure that the path lengths from the lens to the cells are equal. Consequently, it is intended that the claims be interpreted to cover such modifications and equivalents.

What is claimed is:

1. In a differential absorption detector, the improvement comprising:

two tapered gas cells side by side, each cell having the same cross-sectional area at each point along its length as the other cell, said cells being disposed parallel to each other with one effectively a mirror image of the other, means for producing monochromatic light;

means for directing said monochromatic light through said cells and for shaping said light passing through each of said cells into a beam conforming to the shape of said cells, whereby essentially all volume of gas in each of said cells is illuminated, said means for directing said monochromatic light through said cells being comprised of a lens at one end of one cell for focusing said light through said one cell as a converging beam in one direction, a first mirror at the other end of said one cell and a second mirror at the other end of said other cell, a second mirror at the other end of said cell, said first and second mirrors being disposed for directing said light passing, through said one cell into the other cell in the opposite direction as a diverging beam, and a single lens in front of said one cell for focusing said light into a beam conforming to the tapered shape of said one cell, and means for sensing the difference in pressure of gases in said cells while being illuminated by said cells for close coupling thereto, whereby gases in said cells are subjected to maximum illumination with a minimum of unilluminated gas.

2. Apparatus as defined in claim 1 wherein said means for sensing the difference in pressure of gases in said cells is comprised of a chamber disposed between said cells, said chamber having two opposing and parallel metal plates and a parallel flexible diaphragm supported with a minimum of space between said plates with gas space on each side of said diaphragm in said chamber connected to a different one of said cells by a direct minimum length passage of a minimum diameter necessary to transmit pressure vibrations from the cells into said chamber.

3. Apparatus as defined in claim 2 wherein valves for controlling the flow of gases into and out of said cells through passages in the walls of said cells are each provided with a shaft having a portion protruding into the passage through which flow is controlled into the cell, said shaft portion substantially filling the passage into the cell when the valve is closed to minimize gas volume not illuminated by said light beam through the cell.

4. In a differential optoacoustic absorption detector, the improvement comprising:

two isolated and tapered gas cells in parallel, each cell having a small diameter at one end and a larger diameter at its opposite end, and a circular cross section of the same diameter at the same point along the length of each cell;

means for producing a beam of monochromatic light;

two mirrors, one mirror at the small-diameter end of each cell positioned at 45° with respect to the cell axis to direct light exiting one cell through the other cell;

a lens for focusing said beam of light from said light-producing means onto a principal focus point between said mirrors half way between said axes of said cells; and means positioned between said cells for sensing the difference in pressure of gases in said cells while being illuminated by said focused beam of light, whereby gases in said cells are subjected to maximum illumination with a minimum of gas volume.

5. Apparatus as defined in claim 4 wherein said means for sensing the difference in pressure of gases in said cells is comprised of a chamber disposed between said cells, said chamber having two opposing and parallel metal plates and a parallel flexible diaphragm supported with a minimum of space between said plates with gas space on each side of said diaphragm in said chamber connected to a different one of said cells by a direct minimum length passage of a minimum diameter necessary to transmit pressure variations from the cells into said chamber.

6. Apparatus as defined in claim 5 wherein valves for controlling the flow of gases into and out of said cells through passages in the walls of said cells are each provided with a shaft having a portion protruding into the passage through which flow is controlled into the cell, said shaft portion substantially filling the passage into the cell when the valve is closed to minimize gas volume not illuminated by said light beam through the cell.

7. In a differential optoacoustic absorption detector, the improvmeent comprising:

two tapered gas cells side by side, each cell having the same cross-sectional area at each point along its length as the other cell, said cells being disposed parallel to each other with one effectively a mirror image of the other;

means for producing monochromatic light;

means for directing said monochromatic light through said cells and means for shaping said light passing through each of said cells into a beam conforming to the shape of said cells, whereby essentially all volume of gas in each of said cells is illuminated, said means for directing said monochromatic light through said cells including a beam splitting means for dividing said light into two beams and at least one mirror for directing one of said two beams through one of said cells, and said means for shaing beams is comprised of two lenses, one for shaping a beam through each of said cells of substantially the same shape conforming to the shape of said cells, and means for sensing the difference in pressure of gases in said cells while being illuminated by said monochromatic light, said means being positined between said cells for close coupling thereto, whereby gases in said cells are subjected to maximum illumination with aminimum of unilluminated gas.

8. Apparatus as defined in claim 7 wherein said means for sensing the difference in pressure of gases in said cells is comprised of a chamber disposed between said cells, said chamber having two opposing and parallel metal plates and a parallel flexible diaphragm supported with a minimum of space between said plates with gas space on each side of said diaphragm in said chamber connected to a different one of said cells by a direct minimum length passage of a minimum diameter necessary to transmit pressure vibrations from the cells into said chamber.

9. Apparatus as defined in claim 8 wherein valves for controlling the flow of gases into and out of said cells through passages in the walls of said cells are each provided with a shaft having a portion protruding into the passage through which flow is controlled into the cell, said shaft portion substantially filling the passage into the cell when the valve is closed to minimize gas volume not illuminated by said light beam through the cell.

* * * * *